US009084774B2

(12) United States Patent
Buschmann et al.

(10) Patent No.: US 9,084,774 B2
(45) Date of Patent: Jul. 21, 2015

(54) CO-CRYSTALS OF DULOXETINE AND COX-INHIBITORS FOR THE TREATMENT OF PAIN

(71) Applicants: Helmut Heinrich Buschmann, Aachen Walheim (DE); Lluis Sola Carandell, Tarragona (ES); Jordi Benet Buchholz, Tarragona (ES); Jordi Carles Ceron Bertran, Tarragona (ES); Jesus Ramirez Artero, Tarragona (ES)

(72) Inventors: Helmut Heinrich Buschmann, Aachen Walheim (DE); Lluis Sola Carandell, Tarragona (ES); Jordi Benet Buchholz, Tarragona (ES); Jordi Carles Ceron Bertran, Tarragona (ES); Jesus Ramirez Artero, Tarragona (ES)

(73) Assignee: LABORATORIOS DEL DR. ESTEVE, S.A., Barcelona (ES)

( * ) Notice: Subject to any disclaimer, the term of this patent is extended or adjusted under 35 U.S.C. 154(b) by 0 days.

(21) Appl. No.: 13/942,488

(22) Filed: Jul. 15, 2013

(65) Prior Publication Data

US 2014/0024697 A1     Jan. 23, 2014

Related U.S. Application Data

(63) Continuation of application No. 12/991,420, filed as application No. PCT/EP2009/003617 on May 20, 2009, now Pat. No. 8,501,802.

(30) Foreign Application Priority Data

May 21, 2008  (EP) ..................................... 08384009

(51) Int. Cl.
*A61K 31/381* (2006.01)
*C07D 333/20* (2006.01)
*A61K 31/192* (2006.01)

(52) U.S. Cl.
CPC .............. *A61K 31/381* (2013.01); *A61K 31/192* (2013.01); *C07D 333/20* (2013.01)

(58) Field of Classification Search
CPC ............................ A61K 31/381; C07D 333/20
USPC ..................... 514/447, 438; 549/75
See application file for complete search history.

(56) References Cited

U.S. PATENT DOCUMENTS 6,245,802 B1 *   6/2001   Iyengar et al. ................ 514/438

FOREIGN PATENT DOCUMENTS

| WO | WO 2004/078163 A2 | 9/2004 |
| WO | WO 2005/025675 A2 | 3/2005 |
| WO | WO 2007/134168 A2 | 11/2007 |

OTHER PUBLICATIONS

International Search Report issued by the International Searching Authority (ISA/EP) on Jul. 31, 2009, in connection with International Application No. PCT/EP2009/003617.
Shan Ning, et al., "The role of cocrystals in pharmaceutical science." *Drug Discovery Today* May 2008, published Apr. 22, 2008, vol. 13, No. 9-10, pp. 440-446, XP008098804, ISSN: 1359-6446.
Almarsson, Et al.: "Crystal engineering of the composition of pharmaceutical phases. Do pharmaceutical co-crystals represent a new path to improved medicines." *Chemical Communications—Chemcom*, Royal Society of Chemistry, Great Britain, published Jan. 1, 2004, pp. 1889-1896, XP002415977, ISSN: 1359-7345, the whole document.
Trask Andrew V: "An overview of pharmaceutical cocrystals as intellectual property." *Molecular Pharmaceuticals* May-Jun. 2007, vol. 4, No. 3, pp. 301-309, XP008098803, ISSN: 1543-8384, the whole document.
Office Action issued Dec. 11, 2012 in connection with U.S. Appl. No. 12/991,420, filed Mar. 18, 2011.
Amendment in response to the Dec. 11, 2012 Office Action, filed Mar. 11, 2013 in connection with U.S. Appl. No. 12/991,420, filed Mar. 18, 2011.
Notice of Allowance issued Apr. 1, 2013 in connection with U.S. Appl. No. 12/991,420, filed Mar. 18, 2011.
U.S. Appl. No. 12/991,420, filed Jun. 30, 2011, Helmut Heinrich Buschmann et al.

* cited by examiner

*Primary Examiner* — Taofiq A Solola
(74) *Attorney, Agent, or Firm* — John P. White; Cooper & Dunham LLP

(57) ABSTRACT

The present invention relates to co-crystals of duloxetine and co-crystal formers selected from COX-INHIBITORS, processes for preparation of the same and their uses as medicaments or in pharmaceutical formulations, more particularly for the treatment of pain.

6 Claims, 10 Drawing Sheets

CO-CRYSTALS OF DULOXETINE AND COX-INHIBITORS FOR THE TREATMENT OF PAIN

This application is a continuation of U.S. Ser. No. 12/991,420, filed Nov. 5, 2010, §371 national stage of PCT International Application No. PCT/EP2009/003617, filed May 20, 2009, designating the United States, and claims priority of European Patent Application No. 08384009.0, filed May 21, 2008, the contents of each of which are hereby incorporated by reference in their entirety into this application.

The present invention relates to co-crystals of duloxetine and co-crystal formers selected from COX-INHIBITORs, processes for preparation of the same and their uses as medicaments or in pharmaceutical formulations, more particularly for the treatment of pain.

Pain is a complex response that has been functionally categorized into sensory, autonomic, motor, and affective components. The sensory aspect includes information about stimulus location and intensity while the adaptive component may be considered to be the activation of endogenous pain modulation and motor planning for escape responses. The affective component appears to include evaluation of pain unpleasantness and stimulus threat as well as negative emotions triggered by memory and context of the painful stimulus.

In general, pain conditions can be divided into chronic and acute. Chronic pain includes neuropathic pain and chronic inflammatory pain, for example arthritis, or pain of unknown origin, as fibromyalgia. Acute pain usually follows non-neural tissue injury, for example tissue damage from surgery or inflammation, or migraine.

(+)-(S)—N-Methyl-N-[3-(naphthalene-1-yloxy)-3-(2-thienyl)-propyl]amine, having the INN-name Duloxetine and being also described as (+)-(S)-Duloxetine or (S)-Duloxetine is known to be a potent serotonin and norepinephrine reuptake inhibitor (SNRI). Duloxetine is marketed for the treatment of a variety of diseases like anxiety and depression but also including pain, especially diabetic peripheral neuropathy.

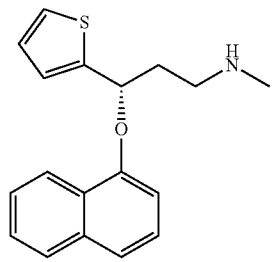

Duloxetine/(S)-Duloxetine

Duloxetine is a commonly used drug. The usual application route is orally with capsules containing duloxetine hydrochloride in enterically coated pellets being applied with doses of 20, 30 and 60 mg of active duloxetine. The enteric coating is necessary as duloxetine is acid labile and therefore would have been in danger to become degenerated in the acid environment of the stomach. The main side effects, nausea, somnolence, insomnia and dizziness, are occurring in 10 to 20% of the patients. In addition a number of severe side-effects have been reported. Being—as said above—a wildly used drug there is a continuous need to improve its properties to achieve a number of effects like improved formulations, higher efficacy, reduction of side effects e.g. through reduction of the necessary doses etc.

Thus it was the objective of the current invention to provide new means of improving the properties of duloxetine, especially in regard to the treatment of pain, by providing new druggable forms of duloxetine.

Especially desirable improvements/advantages of the new druggable form would include:
improvement of physicochemical properties in order to facilitate the formulation, the manufacture, or to enhance the absorption and/or the bioavailability:
thus
being more active when compared to duloxetine base or hydrochloride salt; or
providing a form of duloxetine with a further active agent having a beneficial pharmacological effect in itself, thus allowing for a highly efficient dose/weight relation of the final active principle or even
allowing the use of a lower therapeutic hose of either duloxetine and the further active agent or of both;
having a synergistic effect through the combination of duloxetine and the further active agent in the same new druggable form; or
further
being easily obtainable, easy to manufacture or
allowing more flexibility in formulating, or facilitating its formulation,
being highly soluble, thus allowing better dissolution rates, especially if dissolving in an aqueous physiological surrounding, or
reducing hygroscipicity;
improving stability;
allowing new routes of administration;
also
allowing to combine duloxetine with a chemically usually non-compatible active agent in the same formulation or even in immediate contact, without having to isolate duloxetine; examples would include an acidic active agents and the acid labile duloxetine;
or finally
minimizing/reducing the side effects, especially the severe side effects, assigned to duloxetine.

Most desirably the new druggable forms should combine more than one, or even most of these advantages.

This objective was achieved by providing new co-crystals of duloxetine. It was found that Duloxetine was able to form Co-crystals with COX-INIBITORs. These co-crystals show improved properties if compared to duloxetine alone, and also good analgesic activity. The co-crystals thus obtained have a specific stoichiometry which depends upon the structure of each co-crystal former. Under the proper circumstance this is also another advantage of these new solid druggable forms possibly achieving some modulation of the pharmacological effects. While APIs (Active Pharmaceutical Ingredients) like duloxetine in general have been recognized to form crystalline polymorphs, solvates, hydrates and amorphous forms for a number of years, there is little knowledge about which APIs will form co-crystals. Co-crystals are a specific type of crystalline form which provide a new avenue to modulate the API form and thus to modulate API properties. Co-crystals contain an API and at least one other component which crystallize together. Selection of the other component helps determine whether a co-crystal will form and what properties the co-crystal will have. Just as a polymorph, solvate, hydrate or amorphous form of an API can modulate stability, solubility, and hygroscopicity, a co-crystal can modulate those same properties.

Thus the main object of the present invention is a co-crystal comprising duloxetine and at least one co-crystal former selected from COX-INHIBITORs. The group of COX-INHIBITORs include the NSAIDs (Non steroidal anti-inflammatory drugs).

"COX-INHIBITORs" are defined by the basis of their activity being inhibition of cyclooxygenase (COX), one of the two activities of prostaglandine endoperoxide synthase (PGHS). PGHS is a key enzyme in the prostaglandin pathway. Some preferred co-crystal formers in the sense of this application are those (COX-INHIBITORs/NSAIDs) with a carboxylic acid function, with examples including salicylates, anthranilates, arylacetic acids/arylalkanoic acids, and arylpropionic acids, but also including Coxibs.

"Druggable form (of duloxetine)" as used herein is defined as any form (salt, amorphous crystal, solution, dispersion, mixture etc.) that duloxetine might take which still can be formulated into a pharmaceutical formulation usable as a medicament to treat a disease or a symptom, especially pain.

"Co-Crystal" as used herein is defined as a crystalline material comprising two or more compounds of which at least two are held together by weak interaction, wherein at least one of the compounds is a co-crystal former. Weak interaction is being defined as an interaction which is neither ionic nor covalent and includes for example: hydrogen bonds, van der Waals forces, and π-π interactions. Solvates of duloxetine that do not further comprise a co-crystal former are not co-crystals according to the present invention. The co-crystals may however, include one or more solvate molecules in the crystalline lattice. Just for the sake of clarity the distinction between crystalline salt and a co-crystal has to be stressed here. An API bound to another compound forming a salt by means of ionic interaction can be considered as one "compound" according to the invention, but it cannot be considered as two compounds by itself.

In scientific literature there is currently some discussion on the proper use of the word co-crystal (see for example Desiraju, CrystEngComm, 2003, 5(82), 466-467 and Dunitz, CrystEngComm, 2003, 5(91), 506). A recent article by Zawarotko (Zwarotko, Crystal Growth & design, Vol. 7, No. 1, 2007, 4-9) gives a definition of co-crystal which is in line with the definition given above and thus also is a definition of "co-crystal" according to this invention. According to this article "a co-crystal is a multiple component crystal in which all components are solid under ambient conditions when in their pure form. These components consist of a target molecule or ion and a molecular co-crystal former(s); when in a co-crystal, they coexist at a molecular level within a single crystal."

"Pain" is defined by the International Association for the Study of Pain (IASP) as "an unpleasant sensory and emotional experience associated with actual or potential tissue damage, or described in terms of such damage (IASP, Classification of chronic pain, $2^{nd}$ Edition, IASP Press (2002), 210). Even though pain is always subjective its causes or syndromes can be classified.

According to the IASP "allodynia" is defined as "a pain due to a stimulus which does not normally provoke pain" (IASP, Classification of chronic pain, $2^{nd}$ Edition, IASP Press (2002), 210). Even though the symptoms of allodynia are most likely associated as symptoms of neuropathic pain this is not necessarily the case so that there are symptoms of allodynia not connected to neuropathic pain though rendering allodynia in some areas broader then neuropathic pain.

The IASP further draws the following difference between "allodynia", "hyperalgesia" and "hyperpathia" (IASP, Classification of chronic pain, $2^{nd}$ Edition, IASP Press (2002), 212):

| | | |
|---|---|---|
| Allodynia | Lowered threshold | Stimulus and response mode differ |
| Hyperalgesia | Increased response | Stimulus and response rate are the same |
| Hyperpathia | Raised threshold; Increased response | Stimulus and response rate may be the same or different |

According to the IASP "neuropathy" is defined as "a primary lesion or dysfunction in the nervous system" (IASP, Classification of chronic pain, $2^{nd}$ Edition, IASP Press (2002), 211). Neuropathic pain may have central or peripheral origin.

In one embodiment of the co-crystal according to the invention the co-crystal former or one of the co-crystal formers has at least one functional group from the group consisting of ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, thiocyanate, cyanamide, oxime, nitrile, diazo, organohalide, nitro, s-heterocyclic ring, thiophene, n-heterocyclic ring, pyrrole, o-heterocyclic ring, furan, epoxide, peroxide, hydroxamic acid, imidazole, and pyridine; preferably wherein the co-crystal former has at least one functional group from the group consisting of alcohol, thiol, ester, carboxylic acid, primary amine, secondary amine, tertiary amine.

In one embodiment of the co-crystal according to the invention, the co-crystal former or one of the co-crystal formers has at least one functional group from the group consisting of ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, thiocyanate, cyanamide, oxime, nitrile, diazo, organohalide, nitro, s-heterocyclic ring, thiophene, n-heterocyclic ring, pyrrole, o-heterocyclic ring, furan, epoxide, peroxide, hydroxamic acid, imidazole, and pyridine;

preferably wherein the co-crystal former or one of the co-crystal formers has at least one functional group from the group consisting of alcohol, thiol, ester, carboxylic acid, primary amine, secondary amine, tertiary amine;

most preferably wherein the co-crystal former or one of the co-crystal formers has at least one functional group being a carboxylic acid.

In another embodiment the co-crystal former or one of the co-crystal formers has at least one functional group from the group consisting of alcohol, ester, or carboxylic acid. In a further embodiment the co-crystal former or one of the co-crystal formers has at least one functional group being a carboxylic acid.

In a further embodiment of the co-crystal according to the invention the co-crystal former/s is/are chosen in such a way that if compared to either duloxetine alone or to a mixture of duloxetine and the corresponding active agent/s the solubility of the co-crystal is increased; and/or
the dose response of the co-crystal is increased; and/or
the efficacy of the co-crystal is increased; and/or
the dissolution of the co-crystal is increased; and/or
the bioavailability of the co-crystal is increased; and/or the stability of the co-crystal is increased; and/or the hygroscopicity of the co-crystal is decreased; and/or the form diversity of the co-crystal is decreased; and/or the morphology of the co-crystal is modulated.

"Mixture of duloxetine and the corresponding active agent/s" is defined as a mixture of the active agent or agents in question (the co-crystal former/s) with duloxetine which is only a physical mixture without any coupling interactions between the compounds and thus neither includes salts nor another co-crystal.

The term "salt" is to be understood as meaning any form of duloxetine or the co-crystal former according to the invention in which this assumes an ionic form or is charged and is coupled with a counter-ion (a cation or anion) or is in solution. By this are also to be understood complexes of duloxetine or the co-crystal former with other molecules and ions, in particular complexes which are complexed via ionic interactions. This also includes physiologically acceptable salt.

The term "solvate" according to this invention is to be understood as meaning any form of the duloxetine or co-crystal former in which the compound has attached to it via non-covalent binding another molecule (most likely a polar solvent) especially including hydrates and alcohol solvates, e.g. methanol solvate.

In a further embodiment of the co-crystal according to the invention the molar ratio between duloxetine and the co-crystal former or at least one of the co-crystal formers is different from 1. This might have the advantage of allowing the development of a non-equimolar ratio between duloxetine and the active agent/s in a fixed dose with all the advantages of the co-crystal.

The co-crystal formers are selected from COX-INHIBITORs (which include the NSAIDs), preferably those with a carboxylic acid function. Preferred examples include salicylates, anthranilates, arylacetic acids/arylalkanoic acids, and arylpropionic acids. Therefore, a preferred embodiment of the invention is a co-crystal comprising duloxetine and at least one co-crystal former selected from NSAIDs, preferably from NSAIDs with a carboxylic acid function. Another preferred embodiment of the invention is a co-crystal comprising duloxetine and at least one co-crystal former selected from NSAIDs, selected from salicylates, anthranilates, arylacetic acids/arylalkanoic acids, or arylpropionic acids. Other preferred embodiment of the invention are a) a co-crystal comprising duloxetine and at least one co-crystal former selected from an NSAID being a salicylate; b) a co-crystal comprising duloxetine and at least one co-crystal former selected from an NSAID being a anthranilate; c) a co-crystal comprising duloxetine and at least one co-crystal former selected from an NSAID being an arylacetic acid/arylalkanoic acid; or d) a co-crystal comprising duloxetine and at least one co-crystal former selected from an NSAID being an arylpropionic acid.

Examples of salicylates are: Acetylsalicylic acid, Diflunisal, Ethenzamide, Salicylamide, Triflusal, Fosfosal, and Benorylate. Examples of anthranilates are: Etofenamate, Flufenamic acid, Meclofenamic acid, Mefenamic acid, Niflumic acid, and Tolfenamic acid. Examples of arylacetic acids/arylalkanoic acids are: Acemetacin, Oxametacin, Glucametacin, Proglumetacin, Bufexamac, Diclofenac, Alcofenac, Aceclofenac, Indomethacin, Lonazolac, Sulindac, Tolmetin, Amtolmetin guacil, Mofezolac, Bromfenac, Nabumetone, Fentiazac, and Felbinac. Examples of arylpropionic acids are: Flurbiprofen, Flurbiprofen axetil, Ibuprofen, Ketoprofen, Naproxen, Tiaprofenic acid, Zaltoprofen, Pirprofen, Fenoprofen, Vedaprofen, Nepafenac, Amfenac, and Clidanac.

In a further embodiment of the co-crystal according to the invention the co-crystal former or one of the co-crystal formers is selected from Acetylsalicylic acid, Diflunisal, Ethenzamide, Salicylamide, Triflusal, Fosfosal, Benorylate, Etofenamate, Flufenamic acid, Meclofenamic acid, Mefenamic acid, Niflumic acid, Tolfenamic acid, Acemetacin, Oxametacin, Glucametacin, Proglumetacin, Bufexamac, Diclofenac, Alcofenac, Aceclofenac, Indomethacin, Lonazolac, Sulindac, Tolmetin, Amtolmetin guacil, Mofezolac, Bromfenac, Nabumetone, Fentiazac, Felbinac, Flurbiprofen, Flurbiprofen axetil, Ibuprofen, Ketoprofen, Naproxen, Tiaprofenic acid, Zaltoprofen, Pirprofen, Fenoprofen, Vedaprofen, Nepafenac, Amfenac, and Clidanac; or their stereoisomers, salts or metabolites.

Other examples of NSAIDs are the Coxibs, selective COX-2 Inhibitors. Therefore, another preferred embodiment of the invention is a co-crystal comprising duloxetine and at least one co-crystal former selected from an NSAID being a Coxib. Examples of Coxibs are: Celecoxib, Etoricoxib, Lumiracoxib, Parecoxib, Rofecoxib, Valdecoxib, and Cimicoxib.

Further examples of the co-crystal former are para-aminophenol derivatives. Therefore, another preferred embodiment of the invention is a co-crystal comprising duloxetine and at least one co-crystal former selected from a para-aminophenol derivative. Examples of para-aminophenol derivatives are: Paracetamol, Propacetamol, and Phenidine.

In a further embodiment of the co-crystal according to the invention the co-crystal former or one of the co-crystal formers is selected from Acetylsalicylic acid, Diflunisal, Ethenzamide, Salicylamide, Triflusal, Fosfosal, Benorylate, Paracetamol, Propacetamol, Phenidine, Etofenamate, Flufenamic acid, Meclofenamic acid, Mefenamic acid, Niflumic acid, Tolfenamic acid, Acemetacin, Oxametacin, Glucametacin, Proglumetacin, Bufexamac, Diclofenac, Alcofenac, Aceclofenac, Indomethacin, Lonazolac, Sulindac, Tolmetin, Amtolmetin guacil, Mofezolac, Bromfenac, Nabumetone, Fentiazac, Felbinac, Flurbiprofen, Flurbiprofen axetil, Ibuprofen, Ketoprofen, Naproxen, Tiaprofenic acid, Zaltoprofen, Pirprofen, Fenoprofen, Vedaprofen, Nepafenac, Amfenac, Clidanac, Metamizol, Propylphenazone, Kebuzone, Mofebutazone, Oxyphenbutazone, Phenylbutazone, Apazone, Isoxicam, Lornoxicam, Piroxicam, Tenoxicam, Ketorolac, Proquazone, Oxaprozine, Ditazole, Etodolac, Meloxicam, Nimesulide, Celecoxib, Etoricoxib, Lumiracoxib, Parecoxib, Rofecoxib, Valdecoxib, Cimicoxib; or their stereoisomers, salts or metabolites;

or

Acetylsalicylic acid, Diflunisal, Ethenzamide, Salicylamide, Triflusal, Fosfosal, Benorylate, Paracetamol, Propacetamol, Phenidine, Etofenamate, Flufenamic acid, Meclofenamic acid, Mefenamic acid, Niflumic acid, Tolfenamic acid, Acemetacin, Oxametacin, Glucametacin, Proglumetacin, Bufexamac, Diclofenac, Alcofenac, Aceclofenac, lndomethacin, Lonazolac, Sulindac, Tolmetin, Amtolmetin guacil, Mofezolac, Bromfenac, Nabumetone, Fentiazac, Felbinac, Flurbiprofen, Flurbiprofen axetil, Ibuprofen, Ketoprofen, Naproxen, Tiaprofenic acid, Zaltoprofen, Pirprofen, Fenoprof en, Vedaprofen, Nepafenac, Amfenac, Clidanac, Metamizol, Propylphenazone, Kebuzone, Mofebutazone, Oxyphenbutazone, Phenylbutazone, Apazone, Isoxicam, Lornoxicam, Piroxicam, Tenoxicam, Ketorolac, Proquazone, Oxaprozine, Ditazole, Etodolac, Meloxicam, Nimesulide, Celecoxib, Etoricoxib, Lumiracoxib, Parecoxib, Rofecoxib, Valdecoxib, Cimicoxib; Bermoprofen; Pelubiprofen; Tenosal; Aceneuramic acid; Pirazolac; Xinoprofen; Flobufen; Anirolac; Zoliprofen; Bromfenac; Pemedolac; Dexpemedolac; Bindarit; Romazarit; (S)-Naproxen; Tiaprofenic acid; Fenbufen; Fenoprofen; Flobufen; Oxaprozin; or their stereoisomers, salts or metabolites;

preferably is selected from

Acetylsalicylic Acid; Triflusal; HTB (2-hydroxy-4-trifluoromethyl benzoic acid); Diflunisal; Meclofenamic acid; Mefenamic acid; Niflumic acid; Flufenamic acid; Diclofenac; Lonazolac; Acemetacin; Indomethacin; Tolmetin; Sulindac; Etodolac; Ketorolac; Flurbiprofen; (RS)-Flurbiprofen; Esflurbiprofen; Ibuprofen; (RS)-Ibuprofen; S-(+)-Ibuprofen; Ketoprofen; (rac)-Ketoprofen; R-(−)-Ketoprofen; Bermoprofen; Pelubiprofen; Tenosal; Aceneuramic acid; Pirazolac; Xinoprofen; Flobufen; Anirolac; Zoliprofen; Bromfenac; Pemedolac; Dexpemedolac; Bindarit; Romazarit; Naproxen; (S)-Naproxen; Tiaprofenic acid; Fenbufen; Fenoprofen; Flobufen; Oxaprozin; their stereoisomers or salts;

more preferably is Acetylsalicylic acid, Paracetamol; Naproxen, (S)-Naproxen; Ibuprofen, (RS)-Ibuprofen, S-(+)-Ibuprofen; or one of their salts.

In general, all of these co-crystal formers which have at least one stereogenic center are to be understood as being included herein in their racemic form or as diastereoisomers or enantiomers or mixtures thereof.

A highly interesting COX-INHIBITOR to be the co-crystal former with duloxetine is the marketed drug naproxen, whose chemical name is (S)-(6-methoxy-2-naphtyl)propionic acid, and which is also described as a physiologically acceptable salt. It has an empirical formula of $C_{14}H_{14}O_3$, an Mp of 153° C. and a pKa of 4.2.

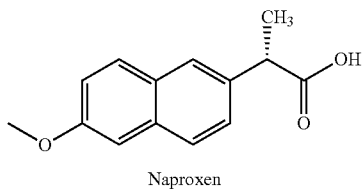 [SMILES: COc1ccc2cc([C@H](C)C(=O)O)ccc2c1]

Naproxen

Thus, another very preferred aspect of the invention relates to a co-crystal according to the invention, wherein the co-crystal former is naproxen, its enantiomers or salts thereof. Especially it refers to a co-crystal according to the invention, wherein the co-crystal former is (S)-naproxen.

As illustrated in more detail below duloxetine forms co-crystals with (S)-naproxen. Generally co-crystals obtained have a specific stoichiometry which depends upon the structure of each co-crystal former. In this specific case of the co-crystal with (S)-naproxen being the co-crystal former the molecular ratio between duloxetine and (S)-naproxen is 2 to 3.

In this specific co-crystal of duloxetine and (S)-naproxen according to the invention the endothermic sharp peak corresponding to the melting point has an onset at 124° C.

This specific co-crystal of duloxetine and (S)-naproxen according to the invention shows an X-Ray powder diffraction pattern with peaks expressed in d-Value in Å at 12.889, 10.733, 10.527, 9.194, 8.541, 7.594, 7.430, 6.656, 6.444, 6.082, 5.975, 5.754, 5.436, 5.346, 5.259, 5.182, 5.131, 4.953, 4.930, 4.817, 4.766, 4.739, 4.690, 4.654, 4.638, 4.597, 4.434, 4.293, 4.266, 4.174, 4.068, 4.005, 3.984, 3.940, 3.886, 3.795, 3.769, 3.735, 3.715, 3.641, 3.577, and 3.533.

This specific co-crystal of duloxetine and (S)-naproxen according to the invention further has a triclinic unit cell with the following dimensions a=10.9284(4) Å
b=12.1480(6) Å
c=13.5613(7) Å
α=107.477(3)°
β=99.792(3)°
γ=95.382(2)°

Another highly interesting COX-INHIBITOR to be the co-crystal former with duloxetine is the marketed drug tolmetin, whose chemical name is [1-methyl-5-(4-methylbenzoyl)-1H-pyrrol-2-yl]acetic acid] and which is also described as a physiologically acceptable salt.

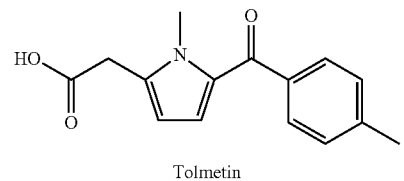 [SMILES: Cc1ccc(C(=O)c2ccc(CC(=O)O)n2C)cc1]

Tolmetin

Thus, another very preferred aspect of the invention relates to a co-crystal according to the invention, wherein the co-crystal former is tolmetin, or salts thereof.

As illustrated in more detail below duloxetine forms co-crystals with tolmetin. Generally co-crystals obtained have a specific stoichiometry which depends upon the structure of each co-crystal former. In this specific case of the co-crystal with tolmetin being the co-crystal former the molecular ratio between duloxetine and tolmetin is 1 to 2.

In this specific co-crystal of duloxetine and tolmetin according to the invention the endothermic sharp peak corresponding to the melting point has an onset at 111° C.

This specific co-crystal of duloxetine and tolmetin according to the invention shows an X-Ray powder diffraction pattern with peaks expressed in d-Value in Å at 13.774, 12.845, 11.510, 9.146, 8.909, 8.462, 7.662, 6.856, 6.435, 6.329, 6.019, 5.881, 5.715, 5.571, 5.259, 5.010, 4.928, 4.888, 4.569, 4.443, 4.274, 4.216, 4.136, 4.032, 3.951, 3.896, 3.830 and 3.757.

In another preferred embodiment of the co-crystal according to the invention the co-crystal former is ibuprofen, its enantiomers or salts thereof.

In a further preferred embodiment of the co-crystal according to the invention the co-crystal former is (S)-ibuprofen.

Another embodiment of the present invention relates to a process for the production of a co-crystal according to the invention as described above comprising the steps of:

(a) dissolving or suspending a co-crystal former in a solvent; and (b) heating the solution or dispersion to a temperature above ambient temperature and below the boiling point of the solution or dispersion;

(c) dissolving together with, or after, or before step (a) duloxetine either as a free base or as a salt in a solvent, (d) adding the solution of (c) to the heated solvent of (b) and mixing them;

(e) cooling the mixed solution/dispersion of step (d) to ambient temperature;

(f) filtering-off the resulting co-crystals.

Another embodiment of the present invention relates to a process for the production of a co-crystal according to the invention as described above comprising the steps of:

either (Alternative I):
(a) dissolving or suspending a co-crystal former in a solvent; and
(b) heating the solution or dispersion to a temperature above ambient temperature and below the boiling point of the solution or dispersion;
(c) dissolving together with, or after, or before step (a) duloxetine either as a free base or as a salt in a solvent,
(d) adding the solution of (c) to the heated solvent of (b) and mixing them;

or (Alternative II):
(a) dissolving or suspending a co-crystal former and duloxetine in a solvent; and
(b) heating the solution or dispersion to a temperature above ambient temperature and below the boiling point of the solution or dispersion;
(d) adding a solvent to the heated solvent of (b) and mixing them;

followed by (for both Alternatives I and II)
(e) cooling the mixed solution/dispersion of step (d) to ambient temperature;
(f) filtering-off the resulting co-crystals.

"Ambient temperature" is defined here as a temperature between 20 and 25° C., preferably being 20° C.

The solvents usable in this process include water or organic solvents, preferably solvents selected from acetone, isobutyl acetate, acetonitrile, ethyl acetate, 2-butanol, dimethylcarbonate, chlorobenzene, butylether, diisopropylether, dimethylformamide, ethanol, water, hexane, isopropanol, methyl ethyl ketone, methanol, methyl t-butyl ether, 3 pentanone, toluene and 1,1,1-trichloroethane, most preferably including alcohols, like ethanol. It is preferable—but not necessary—that the solvents in steps (a) and (c) for Alternative I are identical.

The molecular ratio between duloxetin and the co-crystal former lies between 10:1 to 1:10; preferably 5:1 to 1:5, more preferably from 3:1 to 1:3 and most preferably from 1:1 to 1:2.

Preferably the duloxetine-solution in step (c) (Alternative I) or (a) (Alternative II) has a concentration of between 3 and 0.01 mM.

The parts of the co-crystal according to the invention are well-known drugs with analgesic properties sometimes used for a long time worldwide. Due to this a further object of the present invention is a medicament comprising a co-crystal according to the invention.

Thus the invention also concerns a medicament comprising at least one co-crystal according to the invention as described above and optionally one or more pharmaceutically acceptable excipients.

The invention also relates to a pharmaceutical composition that comprises a therapeutically effective amount of the co-crystal according to the invention in a physiologically acceptable medium. Physiologically acceptable medium is defined as especially comprising pharmaceutically acceptable auxiliary substances (additives/excipients), especially those suitable for a solid pharmaceutical formulation, of which one or more may be part of the pharmaceutical formulation.

The association of two active principles in the same crystal exhibits several advantages. Being linked, they often behave as a single chemical entity, thus facilitating the treatments, formulation, dosage etc. In addition to that, with both duloxetine and the co-crystal formers being active analgesics these co-crystals are highly useful in the treatment of pain, especially also not losing any activity/weight by the addition of pharmacologically useless counterions as in salts with no API. In addition the two active principles are complementing each other in the treatment especially of pain, but possibly also of various other diseases or symptoms. Thus, the co-crystals according to the invention do combine a high number of advantages over the state of the art.

Another advantage is that the association of two active principles into one unique species seems to allow for a better Pharmacokinetic/Pharmacodynamic (PKPD) including also a better penetration of the blood-brain barrier, which helps in the treatment of pain.

In general in most embodiments in which the co-crystals of duloxetine are used (e.g. for the treatment of pain etc.) these co-crystals would be formulated into a convenient pharmaceutical formulation or a medicament. Accordingly a desirable advantage of a co-crystal of duloxetine would show improved pharmaceutical properties and features, especially when compared to the free base or duloxetine hydrochloride. Thus, the co-crystal of duloxetine according to the invention should desirably show at least one, preferably more, of the following features:

to have a very small particle size, e.g. from 300 μm or lower; or
to be and/or remain essentially free of agglomerates; or
to be less or not very hygroscopic; or
to help in formulating controlled release or immediate release formulations; or
to have a high chemical stability; or
if given to a patient
to decrease the inter- and intra-subject variability in blood levels; or
to show a good absorption rate (e.g. increases in plasma levels or AUC); or
to show a high maximum plasma concentration (e.g. $C_{max}$); or
to show decreased time to peak drug concentrations in plasma ($t_{max}$); or
to show changes in half life of the compound ($t_{1/2}$), in whichever direction this change is preferably directed.

The medicament or pharmaceutical compositions according to the present invention may be in any form suitable for the application to humans and/or animals, preferably humans including infants, children and adults and can be produced by standard procedures known to those skilled in the art. The medicament of the present invention may for example be administered parenterally, including intramuscular, intraperitoneal, or intravenous injection, transmucosal or sublingual application; or orally, including administration as tablets, pellets, granules, capsules, lozenges, aqueous or oily solutions, suspensions, emulsions, sprays or as reconstituted dry powdered form with a liquid medium.

Typically, the medicaments according to the present invention may contain 1-60% by weight of one or more of the co-crystals as defined herein and 40-99% by weight of one or more auxiliary substances (additives/excipients).

The compositions of the present invention may also be administered topically or via a suppository.

The daily dosage for humans and animals may vary depending on factors that have their basis in the respective species or other factors, such as age, sex, weight or degree of illness and so forth. The daily dosage for humans preferably is in the range of 5 to 500 milligrams of duloxetine to be administered during one or several intakes per day.

A further aspect of the invention relates to the use of co-crystal according to the invention as described above for the treatment of pain, preferably acute pain, chronic pain, neuropathic pain, hyperalgesia, allodynia or cancer pain, including diabetic neuropathy or osteoarthritis or fibromyalgia. Preferably this use is provided for in form of a medicament or a pharmaceutical composition according to the invention as described above. Also another aspect of the invention relates to the use of co-crystal according to the invention as described above for the manufacture of a medicament or pharmaceutical composition for the treatment of pain, preferably acute pain, chronic pain, neuropathic pain, hyperalgesia, allodynia or cancer pain, including diabetic neuropathy or osteoarthritis or fibromyalgia.

Another object of the current invention is a method of treatment of pain, preferably acute pain, chronic pain, neuropathic pain, hyperalgesia, allodynia or cancer pain, including diabetic neuropathy or osteoarthritis or fibromyalgia, by providing to a patient in need thereof a sufficient amount of a co-crystal according to the invention as described above (or in preferred aspects as will be described below). Preferably the co-crystal according to the invention is provided in physiologically suitable form like e.g. in form of a medicament or a pharmaceutical composition according to the invention as described above.

The present invention is illustrated below with the help of the following figures and examples. These illustrations are given solely by way of example and do not limit the invention.

BRIEF DESCRIPTION OF THE FIGURES

FIG. 1 is showing the structure formed by 3 molecules of (S)-naproxene and 2 molecules of (S)-duloxetine.

The measured crystal was selected using a Zeiss stereomicroscope using polarized light and prepared under inert conditions immersed in perfluoropolyether as protecting oil for manipulation. Crystal structure determination was carried out using a Bruker-Nonius diffractometer equipped with a APPEX 2 4K CCD area detector, a FR591 rotating anode with $Mo_{K\alpha}$ radiation, Montel mirrors as monochromator and a Kryoflex low temperature device (T=100K). Fullsphere data collection omega and phi scans. Programs used: Data collection Apex2 V. 1.0-22 (Bruker-Nonius 2004), data reduction Saint+Version 6.22 (Bruker-Nonius 2001) and absorption correction SADABS V. 2.10 (2003). Crystal structure solution was achieved using direct methods as implemented in SHELXTL Version 6.10 (Sheldrick, Universität Göttingen (Germany), 2000) and visualized using XP program. Missing atoms were subsequently located from difference Fourier synthesis and added to the atom list. Least-squares refinement on $F_o^2$ using all measured intensities was carried out using the program SHELXTL Version 6.10 (Sheldrick, Universitat Gottingen (Germany), 2000). All non hydrogen atoms were refined including anisotropic displacement parameters

Approximately 20 mg of the samples were prepared in standard sample holders using two foils of polyacetate. Powder diffraction patterns were acquired on a D8 Advance Series 2Theta/Theta powder diffraction system using $Cu_{K\alpha}$-radiation in transmission geometry. The system is equipped with a VÅNTEC-1 single photon counting PSD, a Germanium monochromator, a ninety positions auto changer sample stage, fixed divergence slits and radial soller. Programs used: Data collection with DIFFRAC plus XRD Commander V.2.4.1 and evaluation with EVA V.12.0.

Figure 3:
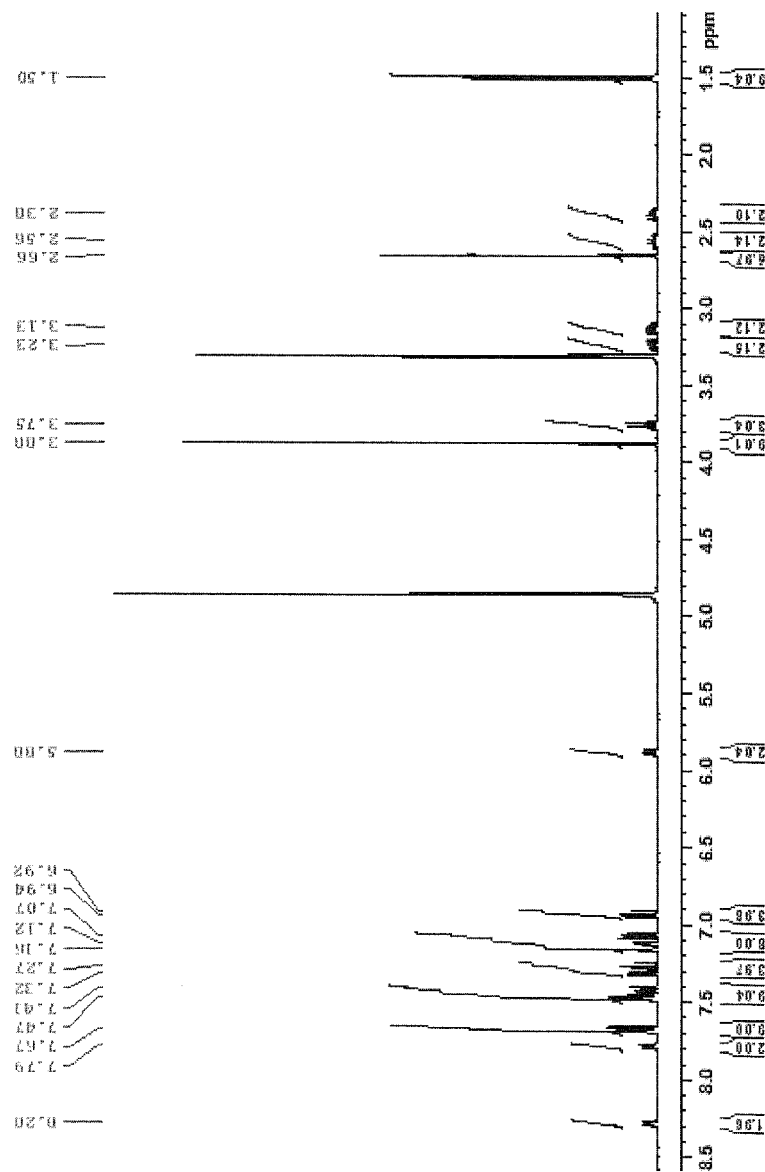

FIG. 3:
$^1$H-NMR of (S)-duloxetine-(S)-naproxene (2:3) co-crystal.

FIG. 3 is depicting a $^1$H-NMR analysis of the co-crystal of (S)-duloxetine and (S)-naproxene showing a 2:3 ratio.

Proton nuclear magnetic resonance analyses were recorded in deuterated methanol (MeOH-d4) in a Bruker Avance 400 Ultrashield NMR spectrometer, equipped with a z-gradient 5 mm BBO (Broadband Observe) probe. Spectra were acquired solving 2-10 mg of sample in 0.6 mL of deuterated solvent.

Figure 4:
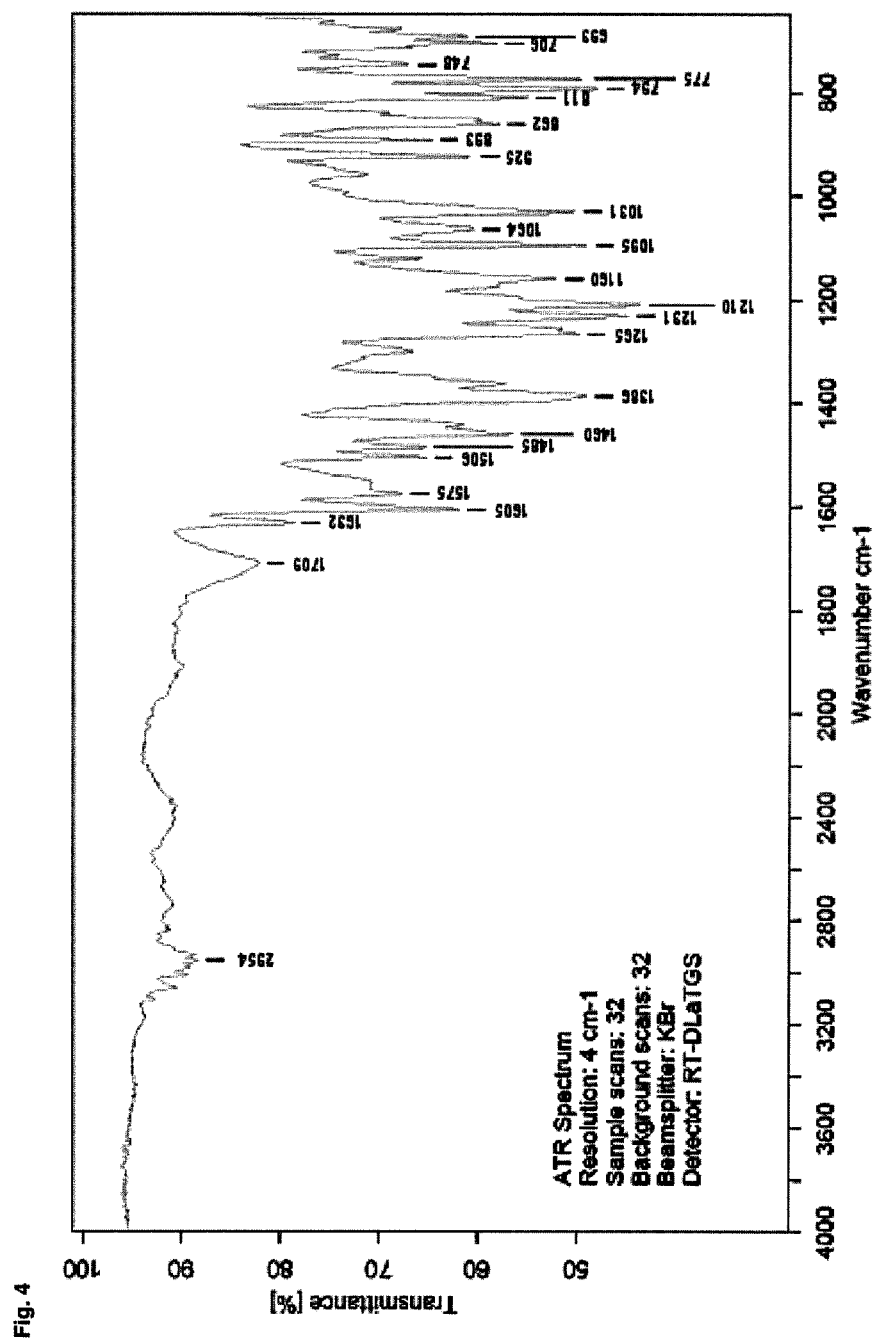

FIG. 4:
FT-IR spectrum of (S)-duloxetine-(S)-naproxene (2:3) co-crystal.

FIG. 4 shows the Infra-red spectrum of the co-crystal obtained.

The FTIR spectra were recorded using a Bruker Tensor 27, equipped with a MKII golden gate single reflection ATR system, a mid-infrared source as the excitation source and a DTGS detector. The spectra were acquired in 32 scans at a resolution of 4 cm$^{-1}$.

Figure 5:
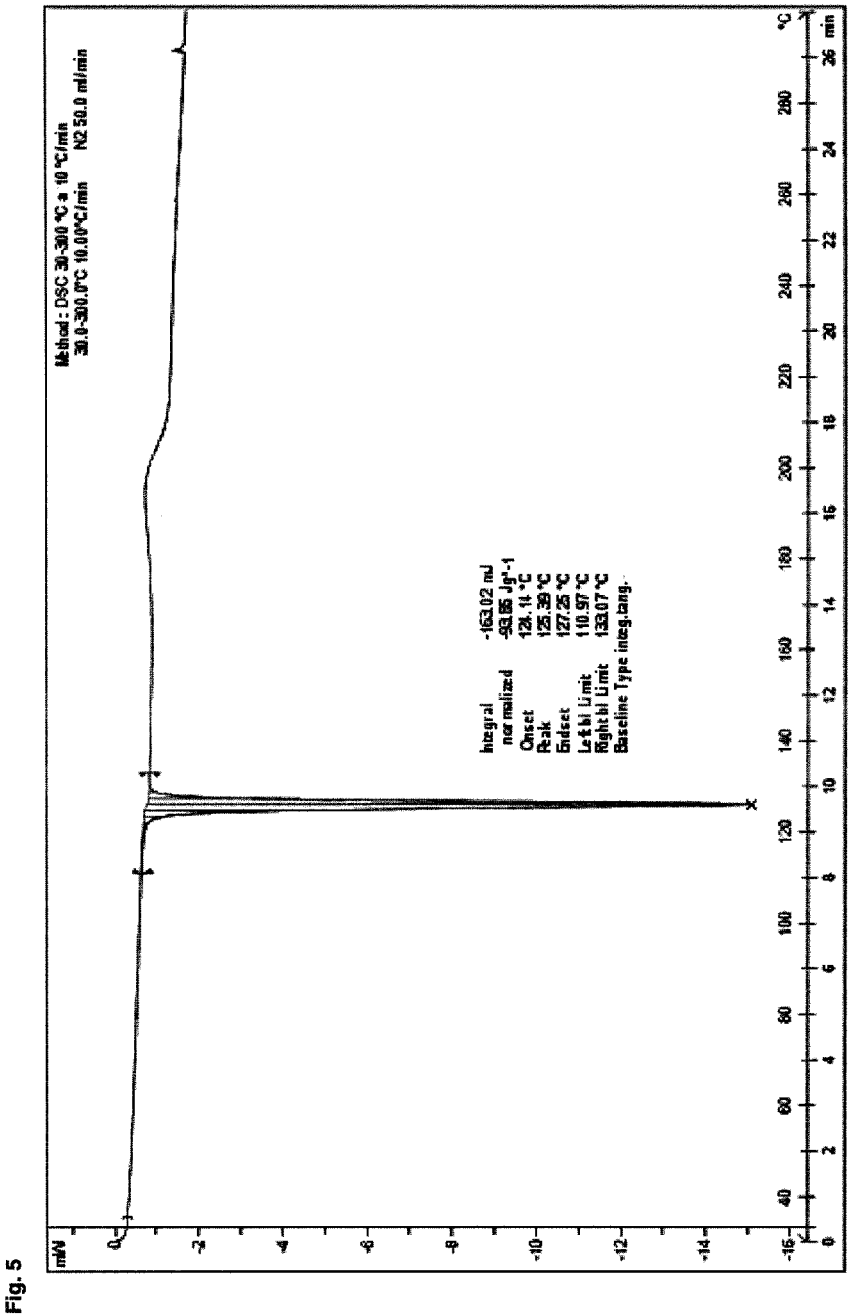

FIG. 5:
DSC analysis of (S)-duloxetine-(S)-naproxene (2:3) co-crystal.

FIG. 5 shows the thermal analysis with a melting point at 124° C. on the DSC.

DSC analyses were recorded in a Mettler Toledo DSC822e. Samples of 1-2 mg were weighted into 40 μL aluminium crucibles with a pinhole lid, and were heated, under nitrogen (50 mL/min), at 10° C./min from 30 to 300° C.

Figure 6:
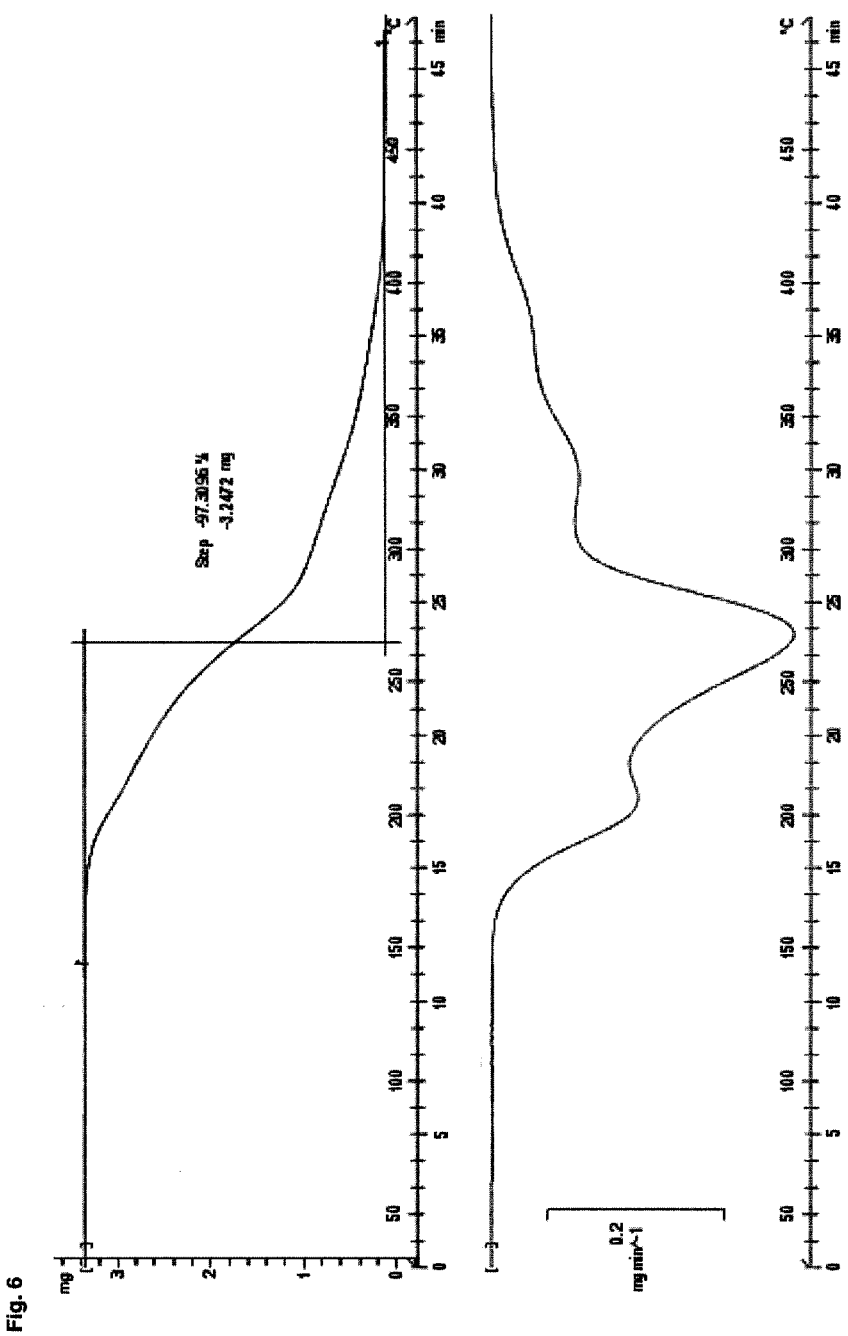

FIG. 6:
TG analysis of (S)-duloxetine-(S)-naproxene (2:3) co-crystal.

FIG. 6 shows the thermogravimetric analysis with no weight-loss at temperatures below decomposition.

Thermogravimetric analyses were recorded in a Mettler Toledo SDTA851e. Samples of 3-4 mg were weighted into 40 μL aluminium crucibles with a pinhole lid, and heated at 10° C./min from 30 to 500° C., under nitrogen (80 mL/min).

Figure 7:
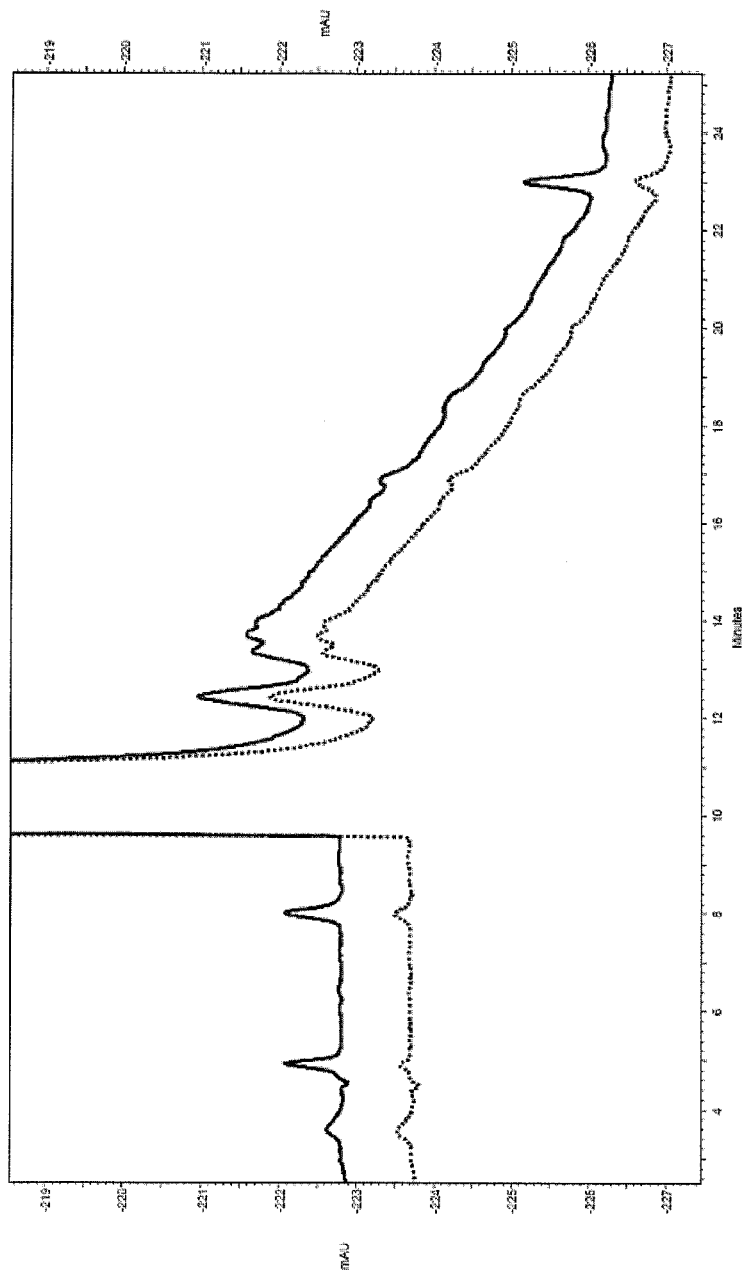

FIG. 7:
Stability study of (S)-duloxetine.HCl as described in Example 1d)

FIG. 7 shows the HPLC chromatogram obtained of the (S)-duloxetine hydrochloride at initial time (dotted line) and after 5 days (solid line).

Figure 8:
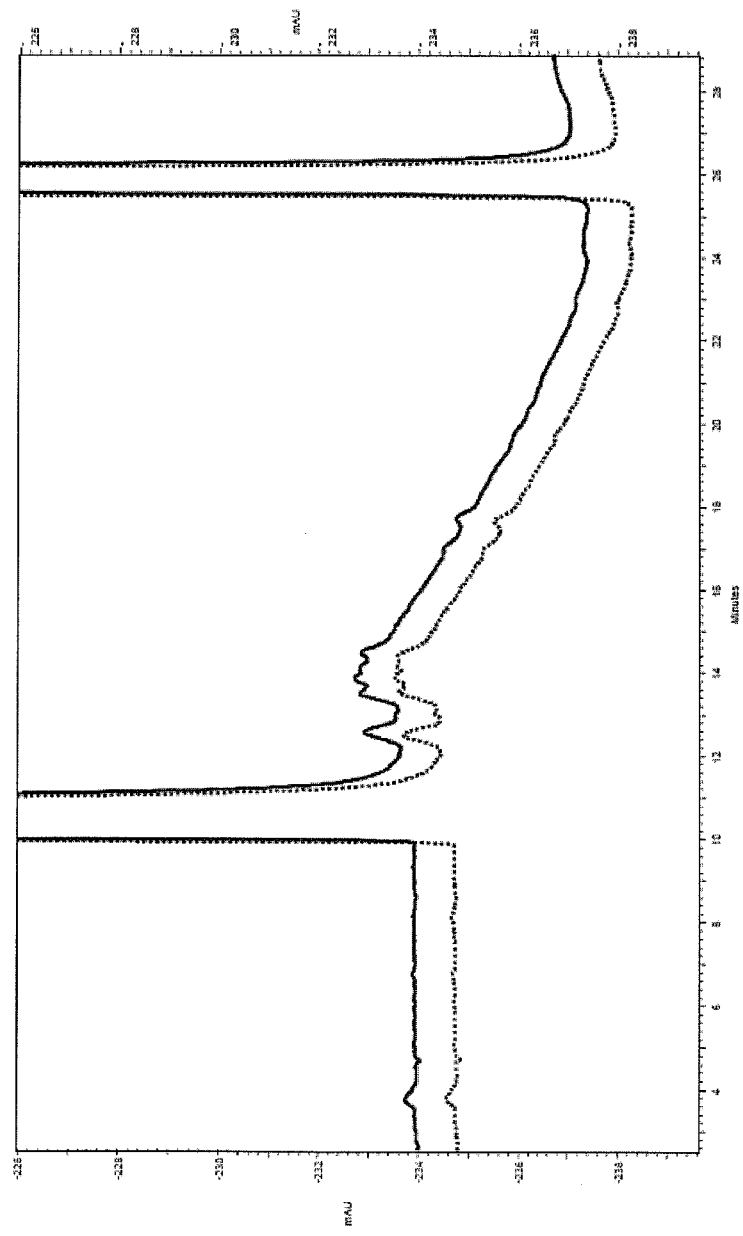

FIG. 8:
Stability study of (S)-duloxetine-(.S)-naproxen (2:3) co-crystal as described in Example 1d) FIG. 8 shows the HPLC chromatogram obtained of the (S)-duloxetine-(S)-naproxen (2:3) co-crystal at initial time (dotted line) and after 5 days (solid line).

Figure 9:
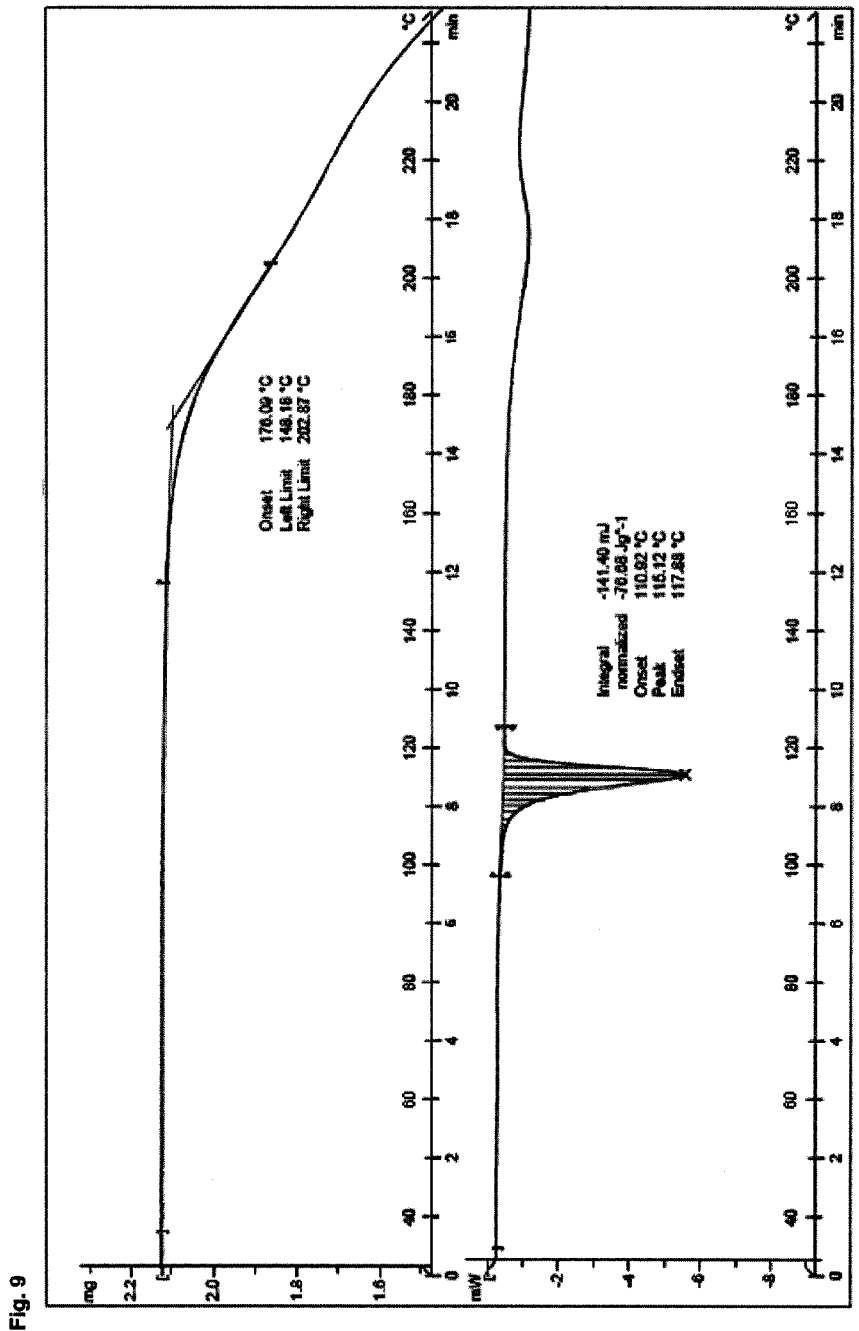

FIG. 9:
DSC analysis of (S)-duloxetine-tolmetin (1:2) co-crystal.
FIG. 9 shows the thermal analysis with a melting point at 111° C. on the DSC.

DSC analyses were recorded in a Mettler Toledo DSC822e. Samples of 1-2 mg were weighted into 40 μL aluminium crucibles with a pinhole lid, and were heated, under nitrogen (50 mL/min), at 10° C./min from 30 to 300° C.

TG analysis of (S)-duloxetine-tolmetin (1:2) co-crystal.
FIG. 9 shows the thermogravimetric analysis with no weight-loss at temperatures below decomposition.

Thermogravimetric analyses were recorded in a Mettler Toledo SDTA851e. Samples of 3-4 mg were weighted into 40 μL aluminium crucibles with a pinhole lid, and heated at 10° C./min from 30 to 500° C., under nitrogen (80 mL/min).

FIG. 10:

Powder X-Ray diffraction pattern of an (S)-duloxetine-tolmetin (1:2) co-crystal.

Approximately 20 mg of the samples were prepared in standard sample holders using two foils of polyacetate. Powder diffraction patterns were acquired on a D8 Advance Series 2Theta/Theta powder diffraction system using $Cu_{K\alpha}$-radiation in transmission geometry. The system is equipped with a VÅNTEC-1 single photon counting PSD, a Germanium monochromator, a ninety positions auto changer sample stage, fixed divergence slits and radial soller. Programs used: Data collection with DIFFRAC plus XRD Commander V.2.4.1 and evaluation with EVA V.12.0.

EXAMPLES

Example 1a

Procedure to Obtain (S)-Duloxetine-(S)-Naproxene (2:3) Co-Crystal

A solution of (S)-duloxetine (472 mg, 1.59 mmol) in 0.4 mL of ethanol was added to a stirred suspension of (S)-naproxene (707 mg, 3.07 mmol, 1.9 eq.) in 0.8 mL of ethanol at 70° C. The resulting solution was left standing at room temperature and a white solid crystallized. The suspension was filtered off and the obtained solid was washed with ethanol and dried under vacuum (10 mm Hg) at 60° C. for 18 hours to give the co-crystal (S)-duloxetine-(S)-naproxene in a 2:3 ratio, as a white crystalline solid (710 mg, 69% yield).

Example 1b

Procedure to Obtain (S)-Duloxetine-(S)-Naproxene (2:3) Co-Crystal

A solution of (S)-duloxetine (26.8 g, 0.09 mol) in 30 mL of ethanol was added to a stirred suspension of (S) naproxene (31.1 g, 0.135 mol, 1.5 eq.) in 50 mL of ethanol at 70° C. The resulting solution was left standing at room temperature and a white solid crystallized. The suspension was filtered off and the obtained solid was washed with ethanol and dried under vacuum (10 mm Hg) at 50° C. for 7 hours to give the co-crystal (S)-duloxetine-(S)-naproxene in a 2:3 ratio, as a white crystalline solid (55.6 g, 96% yield). The co-crystal was the same as the one obtained in example 1a.

Example 1c (S)-duloxetine-(S)-naproxene co-crystal according to examples 1a and 1b has been obtained starting from mixtures of duloxetine ((S)-duloxetine) and (S)-naproxene from 1:1 to 1:2. In addition to the exemplification of examples 1a and 1b different solvents were screened in order to determine the most effective ones to obtain a co-crystal. The following solvents resulted in a co-crystal with duloxetine: acetone, isobutyl acetate, acetonitrile, ethyl acetate, 2-butanol, dimethylcarbonate, chlorobenzene, butylether, diisopropylether, ethanol, water, hexane, isopropanol, methyl ethyl ketone, methanol, methyl-isobutyl ketone, methyl t-butyl ether, 3-pentanone, toluene, DMF, cyclohexane and 1,1,1-trichloroethane. The co-crystal formed in each case was the same as that found in examples 1a and 1b.

Characterisation of the Co-Crystal:

(S)-duloxetine-(S)-naproxene (2:3) co-crystal obtained according to example 1 was fully characterised by $^1$H-NMR, FTIR, X-Ray diffraction, DSC and TG (see FIGS. 1 to 6).

The optical rotation value is of $[\alpha]^{26}_D=+74.5°$ (c=1.00, MeOH)

Figure 1:
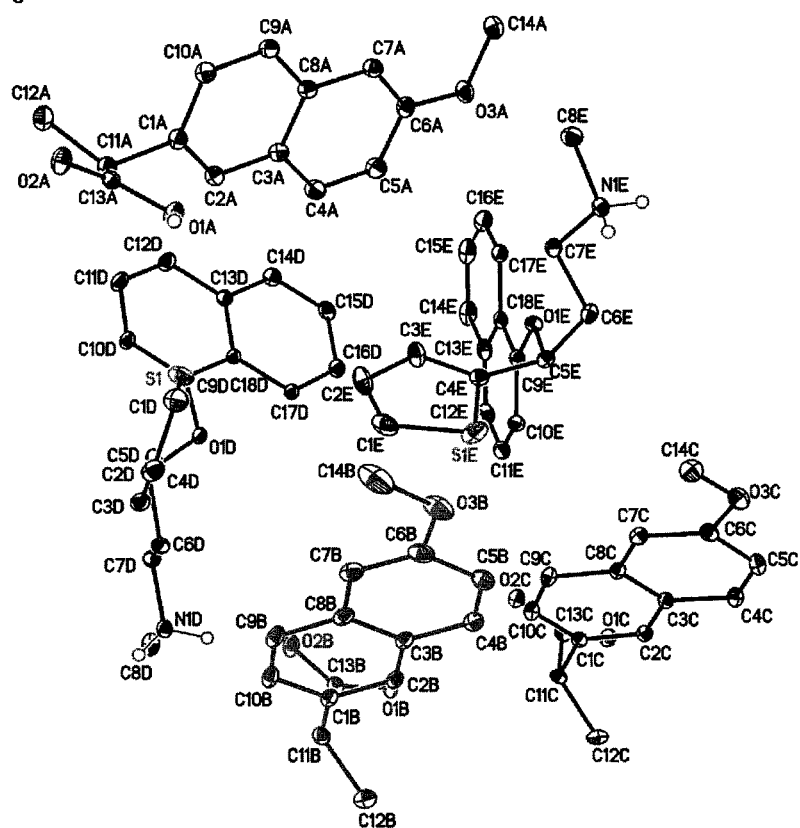
FIG. 1:
Structure of the (S)-duloxetine-(S)-naproxene (2:3) co-crystal obtained by SCXRD analysis. Hydrogen atoms (except attached to heteroatoms) were omitted in the sake of clarity.

The structure was completely determined by single crystal X-ray diffraction (SCXRD) analysis: in FIG. 1 the structure formed by 3 molecules of (S)-naproxene and 2 molecules of (S)-duloxetine is shown. Hydrogen atoms (except attached to heteroatoms) were omitted in the sake of clarity.

Figure 2:
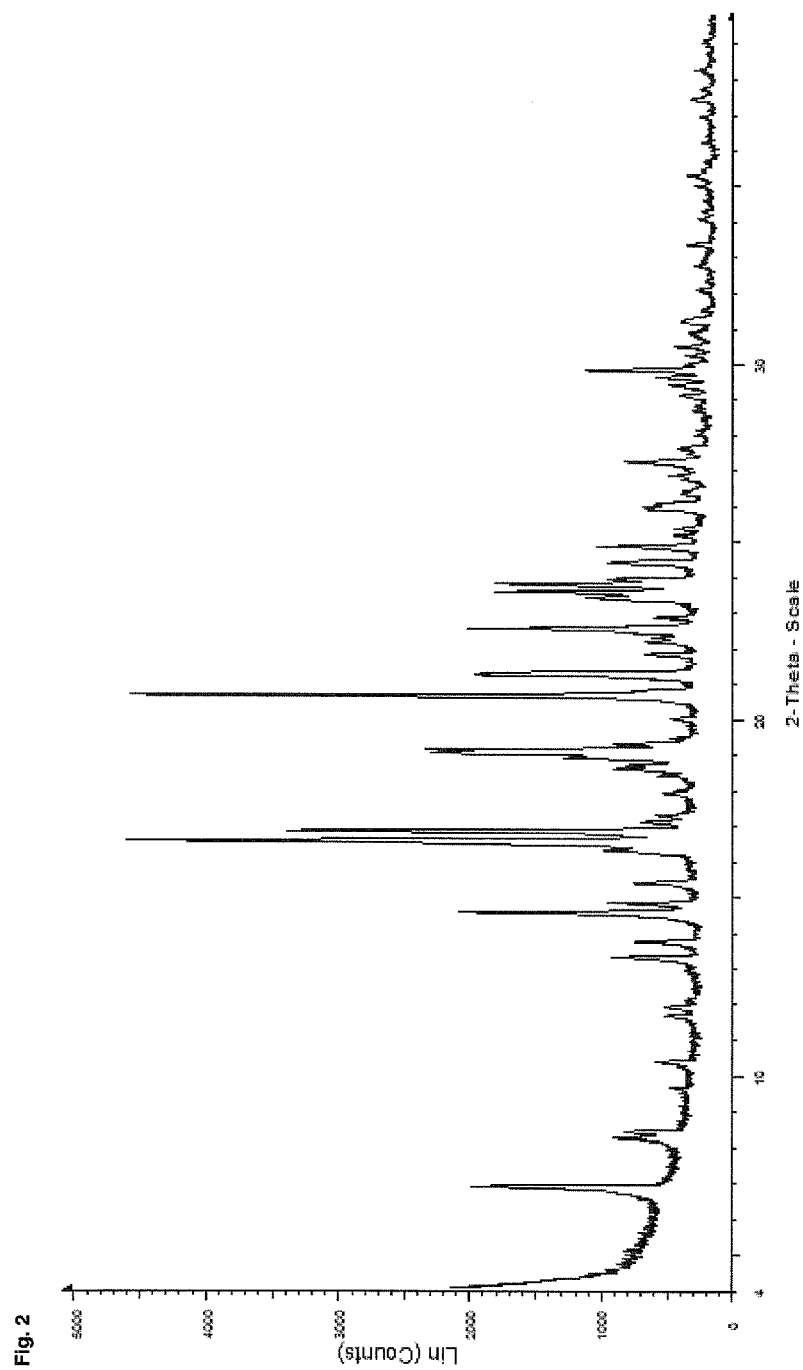
FIG. 2:
Powder X-Ray diffraction pattern of an (S)-duloxetine-(S)-naproxene (2:3) co-crystal.

FIG. 2 shows the Powder X-ray diffraction (PXRD) pattern of the co-crystal of (S)-duloxetine and (S)-naproxen. The peaks expressed in d-value are described in detail in table 2:

TABLE 1

PXRD of a co-crystal of (S)-duloxetine and (S)-naproxen

| Angle 2θ[1] | d-Value (Å) | Relative Intensity % |
|---|---|---|
| 6.852 | 12.88933 | 43.1 |
| 8.231 | 10.73330 | 19.4 |
| 8.392 | 10.52725 | 17.8 |
| 9.612 | 9.19432 | 10.0 |
| 10.349 | 8.54082 | 12.5 |
| 11.644 | 7.59375 | 11.0 |
| 11.902 | 7.42988 | 11.0 |
| 13.291 | 6.65638 | 19.8 |
| 13.730 | 6.44449 | 15.9 |
| 14.551 | 6.08241 | 45.3 |
| 14.815 | 5.97467 | 20.4 |
| 15.387 | 5.75386 | 16.2 |
| 16.294 | 5.43552 | 21.2 |
| 16.568 | 5.34631 | 100.0 |
| 16.845 | 5.25900 | 73.6 |
| 17.099 | 5.18151 | 15.0 |
| 17.269 | 5.13078 | 12.4 |
| 17.894 | 4.95297 | 11.4 |
| 17.979 | 4.92982 | 9.3 |
| 18.405 | 4.81673 | 12.4 |
| 18.601 | 4.76623 | 19.6 |
| 18.708 | 4.73939 | 17.4 |
| 18.907 | 4.68987 | 27.7 |
| 19.053 | 4.65420 | 49.6 |
| 19.120 | 4.63815 | 50.6 |
| 19.291 | 4.59746 | 19.5 |
| 20.009 | 4.43406 | 10.2 |
| 20.671 | 4.29348 | 99.6 |
| 20.807 | 4.26574 | 15.8 |
| 21.269 | 4.17406 | 41.0 |
| 21.831 | 4.06785 | 14.5 |
| 22.180 | 4.00458 | 14.4 |
| 22.294 | 3.98442 | 13.0 |
| 22.549 | 3.94002 | 43.7 |
| 22.867 | 3.88582 | 12.9 |
| 23.422 | 3.79497 | 24.2 |
| 23.585 | 3.76910 | 39.0 |
| 23.807 | 3.73455 | 39.0 |
| 23.935 | 3.71479 | 20.5 |
| 24.427 | 3.64119 | 20.5 |
| 24.871 | 3.57708 | 21.9 |
| 25.187 | 3.53293 | 9.3 |

[1]The 2θ values were obtained using copper radiation ($Cu_{K\alpha}$ 1.54060 Å)

FIG. 3 is depicting a $^1$H-NMR analysis of the co-crystal of (S)-duloxetine and (S)-naproxene showing a 2:3 ratio.

$^1$H NMR (400 MHz, d4-methanol) δ: 1.50 (d, J=7 Hz, 9H), 2.38 (m, 2H), 2.56 (m, 2H), 2.66 (s, 6H), 3.13 (m, 2H), 3.23 (m, 2H), 3.75 (q, J=7 Hz, 3H), 3.88 (s, 9H), 5.88 (dd, J=5 Hz, J=8 Hz, 2H), 6.92 (d, J=8 Hz, 2H), 6.94 (dd, J=3 Hz, J=5 Hz, 2H), 7.07 (dd, J=3 Hz, J=9 Hz, 3H), 7.12 (d, J=3 Hz, 2H), 7.16 (d, J=3 Hz, 3H), 7.27 (t, J=8 Hz, 2H), 7.32 (dd, J=1 Hz, J=5 Hz, 2H), 7.41 (d, J=8 Hz, 2H), 7.44-7.51 (m, 7H), 7.67 (m, 9H), 7.79 (m, 2H), 8.28 (m, 2H).

FIG. 4 shows the Infra-red spectrum of the co-crystal thus obtained.

Thermal analysis shows a melting point at 124° C. on the DSC (FIG. 5) and no weight loss is detected in the TGA at temperatures below decomposition (FIG. 6).

Crystal data and resolve of the structure refinement for (S)-duloxetine-(S)-naproxene (2:3) co-crystal are given in the following table 3:

TABLE 2

Crystal data and resolve of the structure refinement for (S)-duloxetine-(S)-naproxene (2:3) co-crystal.

| | |
|---|---|
| Identification code | p01210napeoh_0m |
| Empirical formula | C78H80N2O11S2 |
| Formula weight | 1285.56 |
| Temperature | 100(2) K |
| Wavelength | 0.71073 Å |
| Crystal system | Triclinic |
| Space group | P1 |
| Unit cell dimensions | a = 10.9284(4) Å    α = 107.477(3)°. |
| | b = 12.1480(6) Å    β = 99.792(3)°. |
| | c = 13.5613(7) Å    γ = 95.382(2)°. |
| Volume | 1672.03(13) Å$^3$ |
| Z | 1 |
| Density (calculated) | 1.277 Mg/m$^3$ |
| Absorption coefficient | 0.144 mm$^{-1}$ |
| F(000) | 682 |
| Crystal size | 0.50 × 0.40 × 0.40 mm$^3$ |
| Theta range for data collection | 2.71 to 39.67°. |
| Index ranges | −19 ≤ h ≤ 19, −20 ≤ k ≤ 10, −24 ≤ l ≤ 23 |
| Reflections collected | 39877 |
| Independent reflections | 23908 [R(int) = 0.0303] |
| Completeness to theta = 39.67° | 83.2% |
| Absorption correction | SADABS (Bruker-Nonius) |
| Max. and min. transmission | 0.9446 and 0.9315 |
| Refinement method | Full-matrix least-squares on F$^2$ |
| Data/restraints/parameters | 23908/3/847 |
| Goodness-of-fit on F$^2$ | 1.028 |
| Final R indices [I > 2sigma(I)] | R1 = 0.0465, wR2 = 0.1115 |
| R indices (all data) | R1 = 0.0650, wR2 = 0.1245 |
| Absolute structure parameter | 0.04(4) |
| Largest diff. peak and hole | 0.583 and −0.427 e.Å$^{-3}$ |

Example 1d

Determination of the Stability of the Co-Crystals According to the Invention

The objective was to measure the stability of the co-crystals of the present invention, and comparing it with the one of the duloxetine HCl. In the literature is described (WO 2007105021) that during stability testing of tablets containing duloxetine, a degradation product is produced in a rearrangement process of the molecule. This process is increased with the presence of strong mineral acids like HCl and HBr. The purpose of the study is perform a comparative stress testing of (S)-duloxetine-(S)-naproxene (2:3) co-crystal at 60° C./75% RH.

Exposure Conditions

Samples of 25 mg of each product are prepared and spread homogeneously on a 5 cm petri dish and stored closed with perforated paper film, inside a climatic chamber Heraeus HC033, during 5 days.

Degradation Products by HPLC

Chromatographic conditions: Column; Sunfire C18, 3.5 um, 100*4.6 mm; Detection: UV 230 nm; Flow: 1 ml/min. Mobile phase: A) 63% (0.02M KH$_2$PO$_4$ at pH of 2.5), 28.8% methanol, 8.2% THF. B) 20% (0.02M KH$_2$PO$_4$ a pH of 2.5), 80% CAN. Gradient: 100% A) 10 min; 100% A) to 25% A) 40 min. Solvent: H$_2$O/ACN, v/v. Concentration: 0.5 mg/ml.

Preparation of Standards

Between 5-5.5 mg of (S)-duloxetine-(S)-naproxene (2:3) co-crystal and (S)-duloxetine.HCl standards, respectively, were weighed with accuracy and dissolved with water, levelling to 10 ml with H$_2$O/ACN, v/v.

Preparation of Test Samples

Between 5-5.5 mg of (S)-duloxetine-(S)-naproxene (2:3) co-crystal and (S)-duloxetine.HCl test samples, respectively, were weighed with accuracy and dissolved with water, levelling to 10 ml with H$_2$O/ACN, v/v.

Solutions are injected by duplicate in above chromatographic conditions.

Assay of each product was calculated by follows:

% assay=(area sample*concentration standard*100)/ (area standard*concentration sample)

Results:

The results obtained are shown in the FIGS. 7 and 8 where the HPLC profiles of each sample at the initial and after 5 days. The results obtained are summarized in the following table 3:

TABLE 3

| | | Impurities and degradation products | | | |
|---|---|---|---|---|---|
| | % assay | Rt. 5 min | Rt. 8 min | Rt. 12.5 min | Rt. 23 min |
| Duloxetine HCl test sample (initial control) | — | 0.01% | 0.01% | 0.15% | 0.03% |
| Duloxetine HCl test sample (5 days control) | 100.9 | 0.05% | 0.05% | 0.15% | 0.07% |
| (S)-duloxetine-(S)-naproxene (2:3) co-crystal test sample (initial control) | — | — | — | 0.03% | — |
| (S)-duloxetine-(S)-naproxene (2:3) co-crystal | 98.2 | — | — | 0.03% | — |

TABLE 3-continued

| | | Impurities and degradation products | | |
|---|---|---|---|---|
| % assay | Rt. 5 min | Rt. 8 min | Rt. 12.5 min | Rt. 23 min |
| test sample (5 days control) | | | | |

Conclusions (S)-duloxetine-(S)-naproxene (2:3) co-crystal is more stable than (S)-duloxetine.HCl in the studied conditions. As it can be observed in the HPLC chromatogram in FIGS. 7 and 8, whereas the (S)-duloxetine-(S)-naproxene (2:3) co-crystal profile does not change after 5 days, in the (S)-duloxetine HCl profile some of the impurities increase.

Example 1e

Determination of the Hygroscopicity of the Co-Crystals According to the Invention The objective was to measure the hygroscopicity of the salts of the present invention, and comparing it with the one of the known salt of each counter part of the salts. The increasing of the weight will be measured in order to evaluate the incorporation of water in the samples, together with the Karl Fischer factor.

According to "Technical guide for the elaboration of monographs" special issue PharmaEuropa, $3^{rd}$ ed., December 1999, the hygroscopicity is defined based on the augmentation of weight after 24 hours of exposition to 80% of relative humidity at 25° C. The scale is the following:

| % incorporation of water | |
|---|---|
| $\Delta < 0.2\%$ | No hygroscopic |
| $0.2\% < \Delta < 2\%$ | Slightly hygroscopic |
| $2\% < \Delta < 15\%$ | Hygroscopic |
| $15\% < \Delta$ | Very hygroscopic |
| Dissolved in water | Deliquescent |

Methods:

Preparation of the Humidity chamber: A supersaturated solution of sodium nitrite (45 g/50 ml) is prepared and introduced in a humidification chamber (samplaterecord). The chamber is maintained at a temperature of 22±2° C. during 24 hours before use, and humidity is controlled each day. Conditioned in that way, the chamber has 64±5% of relative humidity at a temperature of 22±2° C.

Three samples are prepared:
Sample 1: 250 mg of (S)-duloxetine-(S)-naproxene (2:3) co-crystal of example 1,
Sample 2: 115 mg of duloxetine hydrochloride,
Sample 3: 102 mg of sodium naproxen.

The samples are introduced in the conditioned humidity chamber, and the weight is controlled after 24 hours, 48 hours, and 7 days, till an equilibrium is reached (2 successive control with a variation of weight less than 0.2 mg).

The Karl Fischer is also determined (using a Methrom 756 KF) at the beginning and at the end of the study.

Results:

The variation of the weight is controlled and the following percentage is calculated:

$$\Delta\% \text{ weight} = (P_n - P_1)/P_1 \times 100$$

wherein: $P_1$ is the initial weight, $P_n$ in the weight measured for the sample.

The results are summarized in the following table 4:

TABLE 4

| | % of variation of the weight and Karl Fischer value | | | |
|---|---|---|---|---|
| Sample | KF (t = 0) | Δ % weigth 24 h | Δ % weigth 48 h | Δ % weigth 6 days |
| Sample 1 | 0.36 | 0 | 0.09 | 0.13 |
| Sample 2 | 0.33 | 0.19 | 0.26 | 0.18 |
| Sample 3 | 1.04 | 14.39 | 14.39 | 14.3 |

According to the above mentioned scale, whereas the sodium naproxen is hygroscopic, the duloxetine hydrochloride and the (S)-duloxetine-(S)-naproxene (2:3) co-crystal salt of example 1 is not hygroscopic.

Example 2a

Procedure to Obtain (3)-Duloxetine-Tolmetin (12) Co-Crystal

Diisopropyl ether was added drop wise to a solution of (S)-duloxetine (289 mg, 0.97 mmol) and tolmetin (500 mg, 1.94 mmol, 2 eq) in ethyl acetate (1 mL) at reflux until precipitation started. Following, the minimum amount of ethyl acetate was added drop wise to reach complete dissolution again. The solution was then cooled to room temperature, and slowly stirred during 48 h. The resulting suspension was filtered off, washed with cold ethyl acetate and dried under vacuum (10 mm Hg) at 40° C. for 4 hours to give a solid corresponding to a 1:2 ratio (S)-duloxetine-tolmetin co-crystal (700 mg, 89% yield).

Characterization of (S)-Duloxetine-Tolmetin Co-Crystal (1:2 Ratio)

Figure 10:
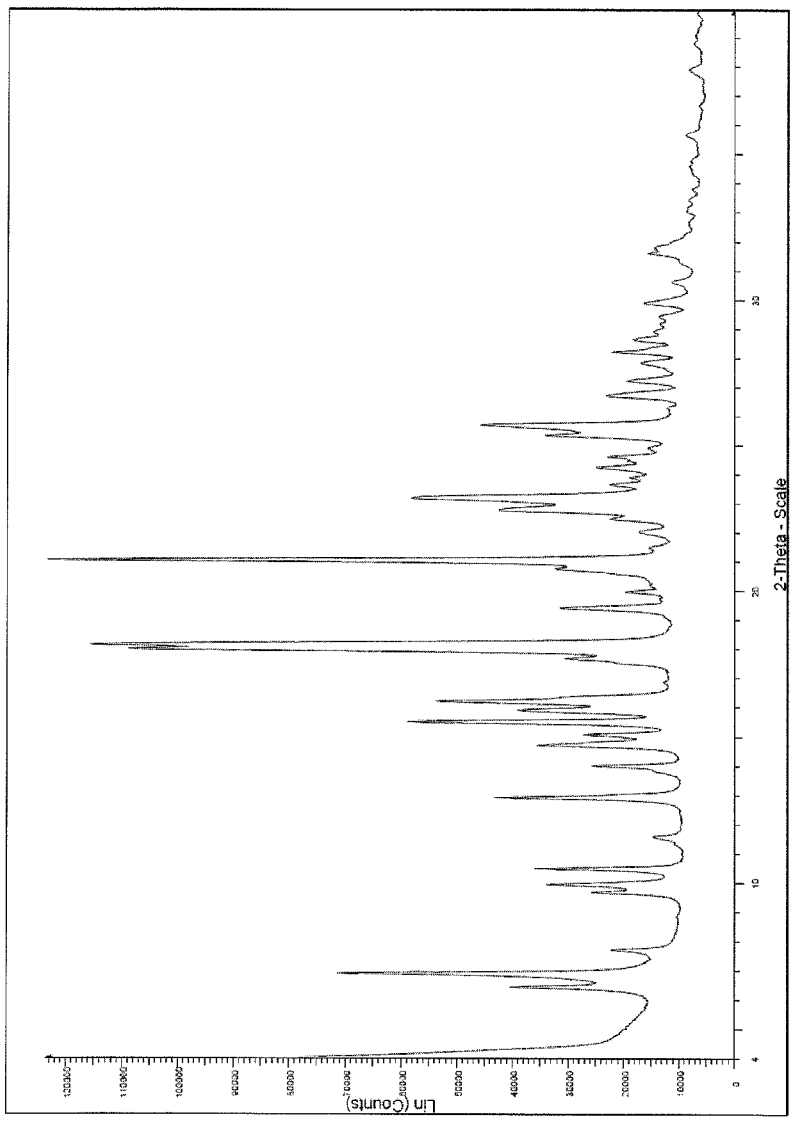

(S)-Duloxetine-tolmetin (1:2) co-crystal obtained according to example 2 was fully characterised by $^1$H-NMR, X-Ray diffraction, DSC and TG (see FIGS. 9 to 10)

$^1$H NMR (400 MHz, d4-methanol) δ: 2.39-2.50 (m, 7H), 2.61 (m, 1H), 2.71 (s, 3H), 3.21 (m, 1H), 3.31 (m, 1H), 3.68 (s, 4H), 3.93 (s, 6H), 5.96 (dd, J=4.6 Hz, J=8 Hz, 1H), 6.10 (d, J=4.1 Hz, 2H), 6.63 (d, J=4.1 Hz, 2H), 6.96 (m, 2H), 7.17 (d, J=3.2 Hz, 1H), 7.28 (m, 4H), 7.33 (d, J=5.2 Hz, 1H), 7.42 (m, 1H), 7.48 (m, 2H), 7.63 (d, J=8 Hz, 4H), 7.79 (m, 1H), 8.30 (m, 1H).

DSC (10° C./min): Endothermic peak corresponding to the melting point with an onset at 111° C. (see FIG. 9).

TG (10° C./min): No weight loss observed at temperatures below the melting point (see FIG. 9).

FIG. 10 shows the Powder X-ray diffraction (PXRD) pattern of the co-crystal of (S)-duloxetine and tolmetin. The peaks expressed in d-value are described in detail in table 5:

TABLE 5

| List of selected peaks obtained by powder X-Ray diffraction of (S)-duloxetine-tolmetin co-crystal. | | |
|---|---|---|
| Angle 2θ[1] (°) | d-value (Å) | Relative intensity % |
| 6.412 | 13.77395 | 32.7 |
| 6.876 | 12.84489 | 57.8 |
| 7.674 | 11.51054 | 17.9 |
| 9.662 | 9.14644 | 20.9 |
| 9.920 | 8.90904 | 27.5 |

TABLE 5-continued

List of selected peaks obtained by powder X-Ray diffraction of (S)-duloxetine-tolmetin co-crystal.

| Angle 2θ[1] (°) | d-value (Å) | Relative intensity % |
|---|---|---|
| 10.446 | 8.46155 | 29.0 |
| 11.539 | 7.66249 | 11.8 |
| 12.903 | 6.85573 | 34.9 |
| 13.750 | 6.43484 | 10.7 |
| 13.982 | 6.32866 | 20.8 |
| 14.706 | 6.01875 | 28.8 |
| 15.051 | 5.88147 | 22.0 |
| 15.493 | 5.71495 | 47.8 |
| 15.896 | 5.57085 | 31.6 |
| 16.844 | 5.25933 | 10.1 |
| 17.689 | 5.01008 | 24.7 |
| 17.987 | 4.92752 | 88.7 |
| 18.133 | 4.88818 | 94.3 |
| 19.410 | 4.56939 | 25.4 |
| 19.965 | 4.44359 | 15.8 |
| 20.766 | 4.27400 | 26.0 |
| 21.054 | 4.21622 | 100.0 |
| 21.467 | 4.13607 | 12.4 |
| 22.029 | 4.03169 | 13.8 |
| 22.486 | 3.95085 | 18.1 |
| 22.805 | 3.89635 | 34.3 |
| 23.207 | 3.82974 | 47.1 |
| 23.664 | 3.75672 | 18.1 |

[1]The 2θ values were obtained using copper radiation ($Cu_{K\alpha 1}$ 1.54060 Å)

The invention claimed is:

1. A co-crystal comprising duloxetine either as a free base or as its physiologically acceptable salt and naproxen as a co-crystal former, wherein the duloxetine either as a free base or as its physiologically acceptable salt and the naproxen are held together by weak interaction; wherein the weak interaction is selected from hydrogen bonds, van der Waals forces and π-π interactions; wherein the naproxen is (S)-naproxen; and wherein the molecular ratio between duloxetine and (S)-naproxen is 2:3.

2. A process for the production of a co-crystal according to claim 1 comprising the steps of:
either (Alternative I):
(a) dissolving or suspending (S)-naproxen in a solvent; and
(b) heating the solution or dispersion to a temperature above ambient temperature and below the boiling point of the solution or dispersion;
(c) dissolving together with, or after, or before step (a) duloxetine either as a free base or as a salt in a solvent,
(d) adding the solution of (c) to the heated solvent of (b) and mixing them;
or (Alternative II):
(a) dissolving or suspending (S)-naproxen former and duloxetine in a solvent; and
(b) heating the solution or dispersion to a temperature above ambient temperature and below the boiling point of the solution or dispersion;
(d) adding a solvent to the heated solvent of (b) and mixing them;
followed by (for both Alternatives I and II)
(e) cooling the mixed solution/dispersion from step
(d) to ambient temperature; and (f) filtering-off the resulting co-crystals.

3. A pharmaceutical composition characterized in that it comprises a therapeutically effective amount of the co-crystal according to claim 1 in a physiologically acceptable medium.

4. A method for the treatment of pain in a subject in need thereof which comprises administering to the subject the pharmaceutical composition of claim 3.

5. A method according to claim 4, wherein the pain is acute pain, chronic pain, neuropathic pain, hyperalgesia, allodynia or cancer pain.

6. A method according to claim 5, wherein the pain is diabetic neuropathy, diabetic peripheral neuropathy, osteoarthritis or fibromyalgia.

* * * * *